(12) United States Patent
Somasundaram et al.

(10) Patent No.: US 12,357,160 B2
(45) Date of Patent: Jul. 15, 2025

(54) MEDICAL DEVICE WITH EXTENDABLE SHAFT

(71) Applicant: Boston Scientific Scimed, Inc., Maple Grove, MN (US)

(72) Inventors: Prashanth Somasundaram, Chicago, IL (US); Jennifer Whelehan, Westborough, MA (US); Rahul Prabhu, Cambridge, MA (US); Tess Davis, Brighton, MA (US); Tara Ann Jarobski, North Oxford, MA (US); Gene Thomas Storbeck, Millis, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 459 days.

(21) Appl. No.: 17/862,543

(22) Filed: Jul. 12, 2022

(65) Prior Publication Data

US 2023/0017488 A1    Jan. 19, 2023

Related U.S. Application Data

(60) Provisional application No. 63/221,116, filed on Jul. 13, 2021.

(51) Int. Cl.
*A61B 1/00* (2006.01)
*A61B 1/005* (2006.01)
(Continued)

(52) U.S. Cl.
CPC .......... *A61B 1/018* (2013.01); *A61B 1/00154* (2013.01); *A61B 1/0052* (2013.01);
(Continued)

(58) Field of Classification Search
CPC ... A61B 1/018; A61B 1/00154; A61B 1/0052; A61B 1/0056; A61B 1/0057; A61B 1/0125; A61M 25/0138; A61M 2025/0004
See application file for complete search history.

(56) References Cited

U.S. PATENT DOCUMENTS 7,322,934 B2 *  1/2008  Miyake .............. A61B 1/00101
                                                         600/173
8,496,574 B2     7/2013  Trusty et al.
(Continued)

OTHER PUBLICATIONS

International Search Report and Written Opinion in International Application No. PCT/US2022/036766, mailed Oct. 21, 2022 (12 pages).

*Primary Examiner* — Timothy J Neal
(74) *Attorney, Agent, or Firm* — Bookoff McAndrews PLLC

(57) ABSTRACT

A medical device may comprise a handle, a first shaft extending from a distal end of the handle, and a second shaft extending a lumen of the first shaft. The handle may further include a first actuator and a second actuator. The first shaft may include (1) a plurality of lumens extending therethrough, (2) a distal face, and (3) a longitudinal axis. Actuation of the first actuator may articulate a distal portion of the first shaft. The second shaft may be axially movable relative to the first shaft such that the second shaft extends out of a distal opening of the first lumen and distally of the distal face. Actuation of the second actuator may articulate a distal portion of the second shaft.

19 Claims, 7 Drawing Sheets

(51) Int. Cl.
   A61B 1/012   (2006.01)
   A61B 1/018   (2006.01)
   A61B 1/05    (2006.01)
   A61B 1/06    (2006.01)
   *A61M 25/00*     (2006.01)
   *A61M 25/01*     (2006.01)

(52) U.S. Cl.
   CPC .......... A61B 1/0056 (2013.01); A61B 1/0057 (2013.01); A61B 1/0125 (2013.01); A61B 1/05 (2013.01); A61B 1/0676 (2013.01); *A61M 2025/0004* (2013.01); *A61M 25/0138* (2013.01)

(56) References Cited

U.S. PATENT DOCUMENTS

| | | | |
|---|---|---|---|
| 2004/0138529 A1* | 7/2004 | Wiltshire | A61B 1/0055 600/144 |
| 2006/0149129 A1 | 7/2006 | Watts et al. | |
| 2006/0189845 A1 | 8/2006 | Maahs et al. | |
| 2007/0177008 A1* | 8/2007 | Bayer | A61B 1/00096 348/65 |
| 2009/0270835 A1* | 10/2009 | Kushner | A61M 25/0136 604/523 |
| 2011/0112622 A1* | 5/2011 | Phan | A61F 2/95 623/1.11 |
| 2018/0160885 A1 | 6/2018 | Abitbol | |
| 2020/0245853 A1 | 8/2020 | Wang et al. | |

* cited by examiner

MEDICAL DEVICE WITH EXTENDABLE SHAFT

CROSS-REFERENCE TO RELATED APPLICATIONS

This patent application claims the benefit under 35 U.S.C. § 119 to U.S. Provisional Patent Application No. 63/221,116, filed on Jul. 13, 2021, the entirety of which is incorporated herein by reference.

TECHNICAL FIELD

Various embodiments of this disclosure relate generally to medical devices for visualization of a target site and delivery of a medical treatment to the target site. Examples of the disclosure relate to a single handle that controls the actuation, rotation, and/or articulation of multiple shafts of the medical device.

BACKGROUND

In some medical procedures, a physician may not have optimal visualization or stability using current devices. For example, during endoscopic retrograde cholangiopancreatography (ERCP) procedures, a physician inserts a first scope to access the target site, and then inserts a second scope to perform cannulation and additional procedures. The operation of two independent scopes creates instability, and requires additional time, user dexterity, and/or multiple users/technicians, for such procedures at the target site.

This disclosure is directed to overcoming one or more of these above-referenced challenges or other challenges in the art.

SUMMARY

Aspects of the disclosure relate to, among other things, medical devices with an extendable shaft. In embodiments, the medical device allows an operator to control multiple degrees of freedom of both a first shaft and a second shaft of the medical device using one handle. Each of the aspects disclosed herein may include one or more of the features described in connection with any of the other disclosed aspects.

According to certain aspects of the disclosure, a medical device may include a handle including a first actuator and a second actuator; a first shaft extending from a distal end of the handle, the first shaft including (1) a plurality of lumens extending therethrough, (2) a distal face, and (3) a longitudinal axis, wherein actuation of the first actuator articulates a distal portion of the first shaft; and a second shaft extending within a first lumen of the plurality of lumens, the second shaft axially movable relative to the first shaft to extend out of a distal opening of the first lumen and distally of the distal face, wherein actuation of the second actuator articulates a distal portion of the second shaft.

The medical device may include one or more of the following features. The second actuator may include a knob, wherein axial movement of the knob in a first direction extends the second shaft relative to the first shaft; axial movement of the knob in a second direction opposite the first direction retracts the second shaft relative to the first shaft; and rotational movement of the knob rotates the second shaft relative to the first shaft. The medical device may include a distal portion of the second shaft comprising a plurality of slots, wherein, when the distal portion is articulated, a proximal face of a first slot meets a distal face of a second slot. The medical device may also include a spring at a distal portion of the second shaft, wherein a proximal end of the spring is fixed axially relative to the first shaft, and wherein a distal end of the spring is fixed to the distal portion of the second shaft. The spring may provide a compressive force on the distal portion of the second shaft to articulate the second shaft when the second shaft extends from the distal face of the first shaft.

According to another aspect of the disclosure, the second actuator may include a button, wherein the button is fixed axially relative to the first actuator, and wherein the button prevents rotational and axial movement of the second shaft relative to the first shaft when the button is depressed, and wherein the button allows rotational and axial movement of the second shaft relative to the first shaft when the button is released.

According to another aspect of the disclosure, the first actuator and the second actuator may be axially fixed relative to each other on the handle. The medical may include a first tube fixedly coupled to the handle and extending from the handle away from the first shaft, wherein the first tube contains a plurality of wires related to the functionality of the first shaft, and a second tube moveably coupled to the handle and extending from the handle away from the first shaft, wherein the second tube contains a plurality of wires related to the functionality of the second shaft, such that the second tube may be pushed into the handle causing a distal portion of the second shaft to extend past the distal face of the first shaft, and such that the second tube may be pulled away from the handle causing a distal portion of the second shaft to retract towards the distal face of the first shaft.

The medical device may alternatively include a first tube fixedly coupled to the handle and extending from the handle away from the first shaft, wherein the first tube contains a plurality of wires related to the functionality of the first shaft, and a second tube moveably coupled to the handle and extending from the handle away from the first shaft, wherein the second tube contains a plurality of wires related to the functionality of the second shaft, such that the second tube may be pushed into the handle causing a distal portion of the second shaft to extend past the distal face of the first shaft, and such that the second tube may be pulled away from the handle causing a distal portion of the second shaft to retract towards the distal face of the first shaft. Additionally, a proximal portion of the second shaft may be configured in a loop, the proximal portion positioned within the handle, and wherein, when the second shaft is extended past the distal face of the first shaft, a diameter of the loop decreases relative to a diameter of the loop when the shaft is retracted into the first shaft.

The handle of the medical device may include at least one port coupled to a proximal portion of a lumen of the first shaft. The handle may also comprise a second port coupled to a proximal portion of a lumen of the second shaft.

According to another aspect of the disclosure, the first shaft may include a camera at the distal face of the first shaft. The distal face of the first shaft may include one or more illumination features. Alternatively or additionally, the second shaft may include a camera at a distal face of the second shaft.

According to another aspect of the disclosure, a medical device may include a handle including a first actuator and a second actuator; a first shaft extending from a distal end of the handle, the first shaft including (1) a plurality of lumens extending therethrough and (2) a distal face, wherein actuation of the first actuator articulates a distal portion of the first shaft; and a second shaft having a longitudinal axis and extending within a first lumen of the plurality of lumens, the second shaft (1) axially movable relative to the first shaft to extend out of a distal opening of the first lumen and distally of the distal face and (2) rotatable about the longitudinal axis relative to the first shaft, wherein actuation of the second actuator selectively articulates a distal portion of the second shaft and rotates the second shaft relative to the first shaft; and wherein axial movement of the second actuator in a first direction may extend the second shaft relative to the first shaft, axial movement of the second actuator in a second direction opposite the first direction retracts the second shaft relative to the first shaft, and rotational movement of the second actuator may rotate the second shaft relative to the first shaft. The medical device may further include a spring at a distal portion of the second shaft providing a compressive force on the distal portion of the second shaft, wherein a proximal end of the spring may be fixed axially relative to the first shaft, and wherein a distal end of the spring may be fixed to the distal portion of the second shaft. The first shaft of this medical device may include a camera at the distal face of the first shaft, and the second shaft may include a camera at a distal face of the second shaft.

According to another aspect of the disclosure, a medical device may include a handle including a first actuator and a second actuator, wherein the first actuator and the second actuator are axially fixed relative to each other. A first shaft may extend from a distal end of the handle, and the first shaft may include (1) a plurality of lumens extending therethrough, (2) a distal face, and (3) a longitudinal axis, wherein actuation of the first actuator may articulate a distal portion of the first shaft. The device may further include a second shaft extending within a first lumen of the plurality of lumens. The second shaft may be axially movable relative to the first shaft to extend out of a distal opening of the first lumen and distally of the distal face. Actuation of the second actuator may articulate a distal portion of the second shaft. A first camera may be fixedly coupled to a distal face of the second shaft. Additionally, the second shaft may be extended by pushing a tube into the handle, causing a distal portion of the second shaft to extend past the distal face of the first shaft, wherein the tube contains a plurality of wires related to the functionality of at least the second shaft.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated herein and constitute a part of this specification, illustrate exemplary aspects of the disclosure and, together with the description, explain the principles of the disclosure.

DETAILED DESCRIPTION

Aspects of the disclosure include devices and methods to enable increased visualization via the extension and articulation of a medical device (e.g., an endoscope) camera. In embodiments, the handle is configured so that a user may control the rotation, articulation, extension, and/or retraction of an endoscope camera by means of one or more actuators within the handle.

The medical device may be introduced into a body cavity or lumen, for example the GI tract, via a natural orifice. The orifice can be, for example, the nose, mouth, or anus, and the placement can be in any portion of the GI tract, including the esophagus, stomach, duodenum, large intestine, or small intestine. Delivery and placement also can be in other body lumens or organs reachable via the GI tract, a natural opening or other body tract, or a bodily incision.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Reference will now be made in detail to examples of the disclosure described above and illustrated in the accompanying drawings. Wherever possible, the same reference numbers will be used throughout the drawings to refer to the same or like parts.

Figure 1:
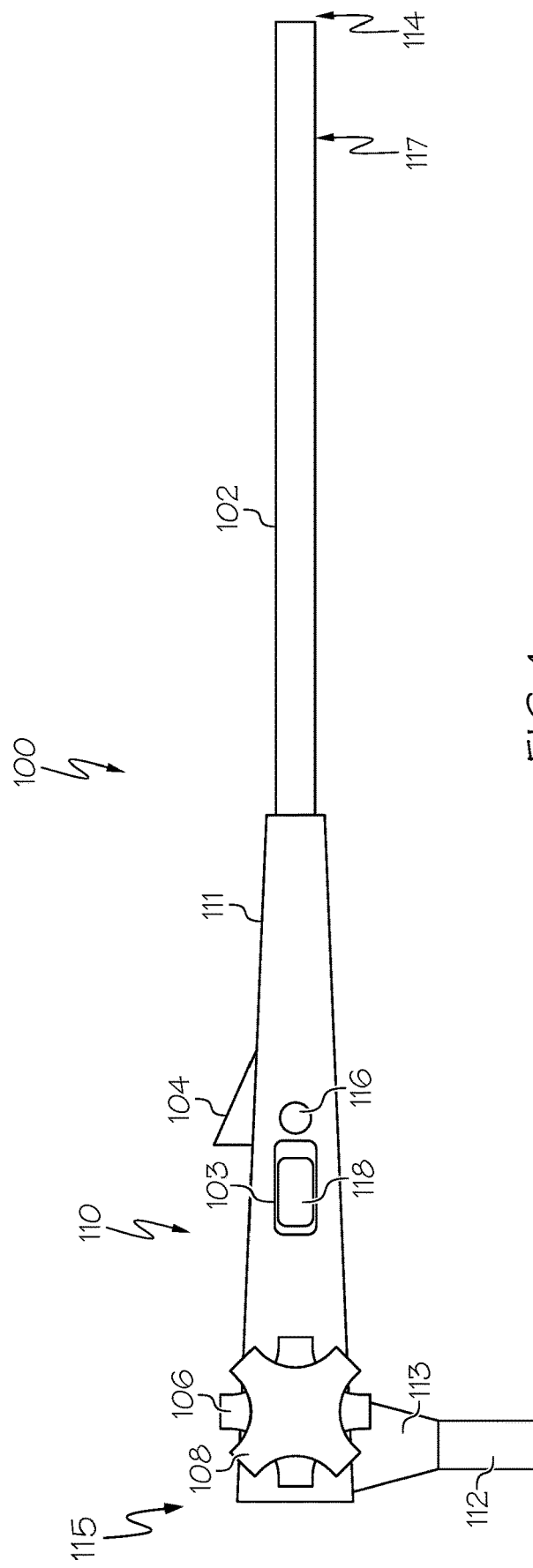
FIG. 1 is a side view of a medical device, according to aspects of this disclosure.

FIG. 1 is a general depiction of medical device 100 in accordance with examples of this disclosure. Medical device 100 includes a proximal end 115 and a distal end 114. A handle 110, including one or more actuators 106, 108, 116, and 118, is at or adjacent to proximal end 115. The handle 110 includes a handle shell 111 housing internal components of handle 110. A strain relief 113 extends perpendicularly from handle 110 relative to a central axis that extends from the proximal end 115 of device 100 to distal end 114. A proximal end of a lumen 112 extends from a distal end of strain relief 113 and may be connected to a processing unit (not pictured) on the distal-most end of lumen 112. A shaft 102 of device 100 extends from a distal end of handle 110 to the distal end 114 of device 100. Distal end 114 includes a distal articulable section 117 of shaft 102, to be described further therein.

Medical device 100 may include a port 104 located at or adjacent to the proximal end of a lumen (e.g. working channel) (not pictured) that extends from the proximal end of shaft 102 to the distal end of shaft 102. Any diagnostic or therapeutic instrument or tool may be inserted into port 104 and extended through the working channel and out of the distal end of shaft 102. Exemplary instruments and tools include, but are not limited to, a tissue grasper, a knife, biopsy forceps, scissors, a retrieval device (such as a net or a basket), an electrocautery tool, etc. Any structures of the medical devices described herein can be made of biocompatible materials, including biocompatible polymers, rubbers, plastics, and the like.

Still referring to FIG. 1, actuators 106, 108, 116, and 118 control various functions at distal end 114. Articulation may be in two planes, such as up-down and left-right. These actuators may include knobs, triggers, buttons, switches, pneumatic controls, or other actuators known in the art and any combination thereof. For example, actuators 106, 108 may control the articulation (bending) of distal end 114 of medical device 100, via a connection between actuators 106, 108 and distal end 114, such as pulls wires. Additionally, actuator 118 may control the extension and rotation of a second shaft (not shown) relative to shaft 102; and actuator 116 may control a braking mechanism of the second shaft (not shown) relative to shaft 102. The actuation of a distal end of an internal shaft (shown in FIG. 2 as internal shaft 120) may be controlled by actuators 116, 118 via a connection between actuators 116, 118 and the distal end of the internal shaft. Articulation may be in two planes, such as up-down and left-right.

Shaft 102 of medical device 100 may be introduced into the body via an incision or natural orifice (i.e. mouth, anus). Shaft 102 may be a tube having sufficient length to access sites within the body. Additionally, shaft 102 may have sufficient flexibility to traverse tortuous anatomy. Shaft 102 can be made of flexible materials, rigid materials, or any combination thereof.

Distal end 114 is at or adjacent to the distal end of shaft 102. Distal end 114 includes a distal articulable section 117 of shaft 102 (e.g. an articulation joint). As mentioned above, and as will be described in further detail below, various handle actuators (e.g. actuators 106, 108, 116, 118) and related mechanisms can control the articulation of articulation section 117 and the rotation, articulation, and extension/retraction of an internal shaft (such as shaft 120), to be described further herein. A connection between the actuators and the distal components, such as one or more elongate members (e.g. wires, cables, etc.) (not pictured), including any connection commonly known in the art, transmit the action of the actuators to the respective functionality at the distal end 114.

Figure 2A:
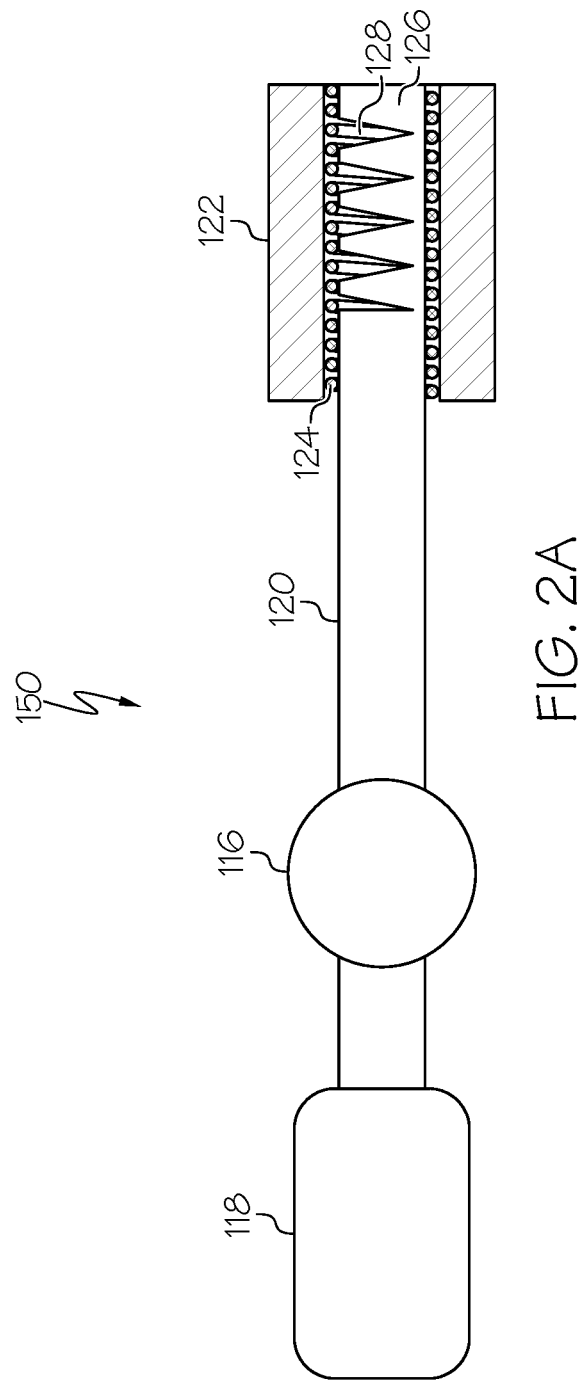
FIGS. 2A and 2B are side views of an exemplary subassembly mechanism that may control the rotation, extension, and articulation of an independent internal camera cable, in the retracted state (FIG. 2A) and in the extended state (FIG. 2B), according to aspects of this disclosure.
Figure 2B:
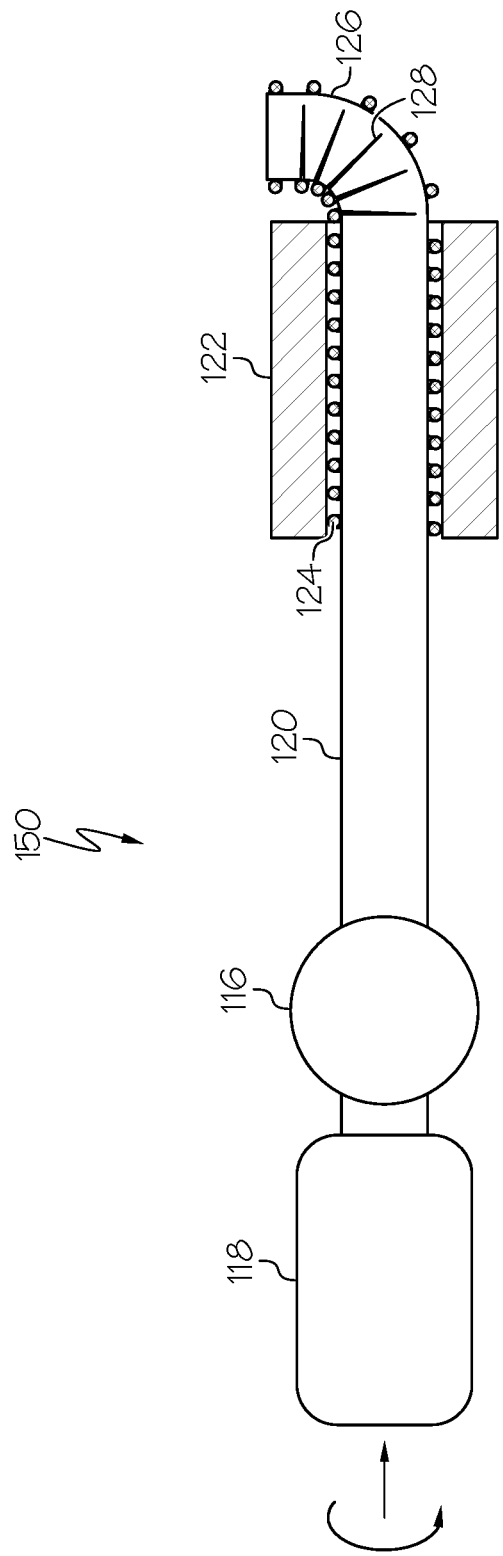

FIGS. 2A and 2B show an exemplary subassembly 150 in a retracted configuration (FIG. 2A) and in an extended, articulated configuration (FIG. 2B). Subassembly 150 may control the rotation, articulation, retraction, and extension of an second, internal shaft 120 within medical device 100.

Subassembly 150 is comprised of actuators 118, 116, internal shaft 120, spring 124, and joint 126 having slots 128. Internal shaft 120 may be coupled to actuator 118 such that, when actuator 118 is rotated or pushed/pulled along a center axis that extends from the proximal end of internal shaft 120 to the distal end of internal shaft 120, internal shaft 120 rotates and translates accordingly. Actuator 118 can be a knob, slider, or any other type of suitable actuator. Actuator 118 is at least partially housed within handle shell 111, and is exposed via a slot 103 in handle shell 111. Actuator 118 translates and rotates within slot 103.

Actuator 116 is spaced distally from actuator 118 such that, when actuator 118 is pushed distally along the axis relative to internal shaft 120, actuator 118 may approach or touch a proximal end of actuator 116. Additionally, internal shaft 120 extends through actuator 116. Actuator 116 may be a braking mechanism for internal shaft 120. A user applying a pressure to the actuator may actuate actuator 116. The application of pressure to actuator 116 may lock the internal shaft 120 in place, preventing the internal shaft 120 from rotating, extending, and/or retracting relative to shaft 102. In an alternative embodiment, actuator 116 may be spring loaded such that the position of the internal shaft 120 is in the locked position until actuator 116 is pressed to release the internal shaft 120.

Internal shaft 120 may be a tube having sufficient length to extend past the distal end of device 100 to access sites within the body. Further, internal shaft 120 may have sufficient flexibility to traverse tortuous anatomy. Internal shaft 120 can be made of flexible materials, rigid materials, or any combination thereof. Internal shaft 120 may also include a tube through which additional tubes and/or cables may extend. Internal shaft 120 may be comprised of one or more camera cables, leading to a camera/imaging device at a distal end of internal shaft 120.

Still referring to FIGS. 2A and 2B, spring 124 surrounds a portion of a distal end of internal shaft 120, including joint 126. Spring 124 may provide support for joint 126 in an articulated state by applying a compressive force on the internal shaft 120. A proximal end of spring 124 may be fixedly coupled to a wall 122 defining a lumen of shaft 102, the lumen defining a channel for shaft 120 to translate and rotate within. A distal end of spring 124 may be fixedly coupled to a distal end of joint 126. These connections (spring 124 to wall 122 and to joint 126) may be accomplished using adhesives, ultrasonic welding, a mechanical fit, or other means known in the art.

Joint 126 is at or adjacent to the distal most end of internal shaft 120. Joint 126 includes a plurality of slots 128 to enable articulation of the distal end of internal shaft 120 in at least one direction. The plurality of slots 128 may be triangular or otherwise shaped to permit articulation of the distal end in at least one direction. Specifically, when the distal portion is articulated, a proximal face of a first slot meets a distal face of a second slot. The slots may be laser cut or otherwise machined into joint 126. Alternatively, joint 126 may be comprised of a plurality of individual links (not shown) configured to permit articulation of the distal end of shaft 120 in at least one direction. The amount of articulation of the internal shaft 120 may be controlled by the shape or geometry of the slots 128 or of the individual links. For example, a slot shaped as an acute triangle could enable a smaller amount of articulation per slot than a slot shaped as an obtuse angle. Further, the number of slots 128 may dictate the amount of articulation achieved. For example, more articulation may be achieved by increasing the number of slots 128, and less articulation may be achieved by decreasing the number of slots 128.

FIG. 2B depicts the internal shaft 120 of subassembly 150 in the extended, articulated state. In this configuration, actuator 118 is pushed distally along the longitudinal axis of internal shaft 120, towards actuator 116. Internal shaft 120 extends through actuator 116 and wall 122. Because a proximal end of spring 124 is coupled to wall 122, and the distal end of spring is coupled to the distal-most end of internal shaft 120, the compressive force exerted on internal shaft 120 by spring 124 in the extended state pulls the walls of slots 128 towards each other, thereby articulating joint 126. In FIG. 2B, joint 126 is bent so that a distal face of shaft 120 faces approximately 90 degrees from an axis of the main portion of shaft 120, so that a camera on the distal face faces to the side of device 100.

Figure 3:
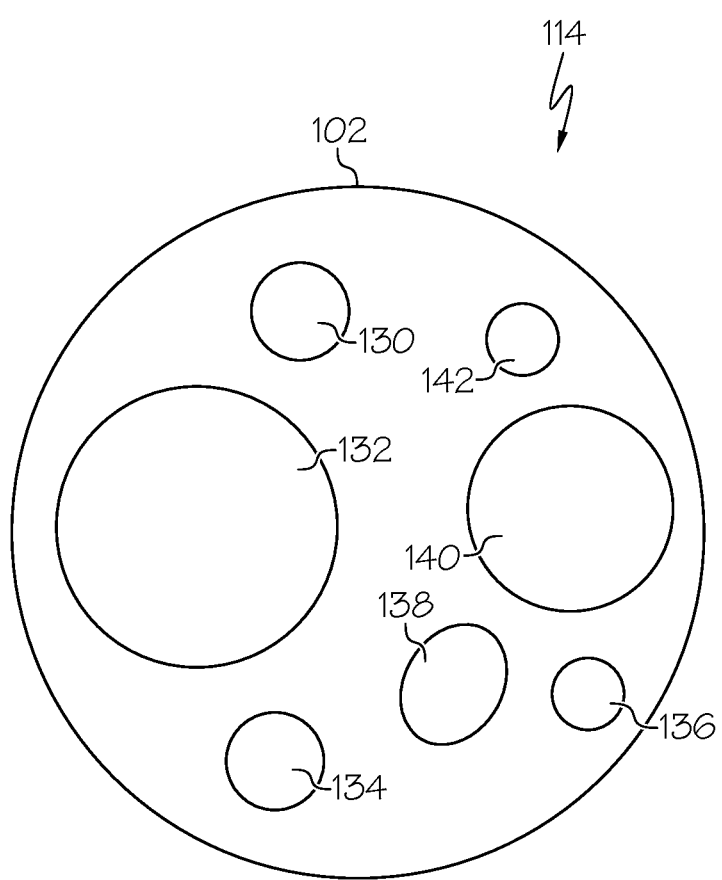
FIG. 3 is an end view of a distal end of the medical device, according to aspects of this disclosure.

FIG. 3 shows an exemplary end view of distal end 114 of shaft 102, shown in FIG. 1. Distal end 114 may be comprised of a plurality of lumens 130, 132, 134, 136, 138, 140, 142, leading to openings at the distal face of shaft 102. Each of the plurality of lumens may have a circular cross-sectional shape or may be defined by any other shape commonly known in the art. Further, any combination of shapes is permitted. For example, lumen 140 may be circular, and lumen 138 may be ovular. Lumen 130 may define a suction or insufflation channel, for providing suction or insufflation at the treatment site. Lumen 132 may define the working channel extending from port 104, through which a tool or instrument may be inserted. Lumen 134 may define a water-jet channel for providing irrigation at then treatment site. Lumen 138 may define a lens wash channel for providing water, saline, or the like to wash lenses of a camera assembly. Lumen 140 may define the camera channel, for receiving shaft 120. Lumens 136 and 142 may define light source channels, for components to provide light to the treatment site. Alternatively or additionally, lights may be provided on and/or within shaft 120, so that light is directed to the treatment site from which an image is taken. The function of each of the lumens shown in FIG. 3 is not limited to those described, however. For example, lumen 130 may define a light source lumen; lumen 132 may define a camera lumen, and so forth, and/or the lumens may provide for other functionality not described herein. The proximal end of the plurality of lumens 130, 132, 134, 136, 138, 140, 142 may be coupled to individual tubes (not shown) that extend through shaft 102 to handle 110 of FIG. 1. Alternatively, the plurality of lumens 130, 132, 134, 136, 138, 140, 142 may define a single flexible extrusion that extends from the distal end of handle 110 to distal end 114. Further, the orientation and quantity of lumens is not limited. Specifically, lumens 130, 132, 134, 136, 138, 140, 142 may be oriented in any manner, and there may be fewer or more lumens, as desired.

Aspects of the disclosure include methods of using device 100. To do so, the user may first introduce the distal end 114 of device 100 into a GI tract via a natural orifice. The orifice can be, for example, the nose, mouth, or anus, and the placement can be in any portion of the GI tract, including the esophagus, stomach, duodenum, large intestine, or small intestine. Delivery and placement also can be in other body lumens or organs reachable via the GI tract, any other natural opening or body tract, bodily incision, or through a delivery device, such as an endoscope or sheath. Once the desired site is accessed, the user can actuate one or more actuators, including knobs 106, 108, to control the articulation of the distal end 114. Further, a user may actuate actuator 118 to rotate, extend, and/or retract shaft 120 of device 100. Actuator 116 may be used to stop shaft 120 or otherwise hold shaft 120 in a desired orientation/position.

Figure 4:
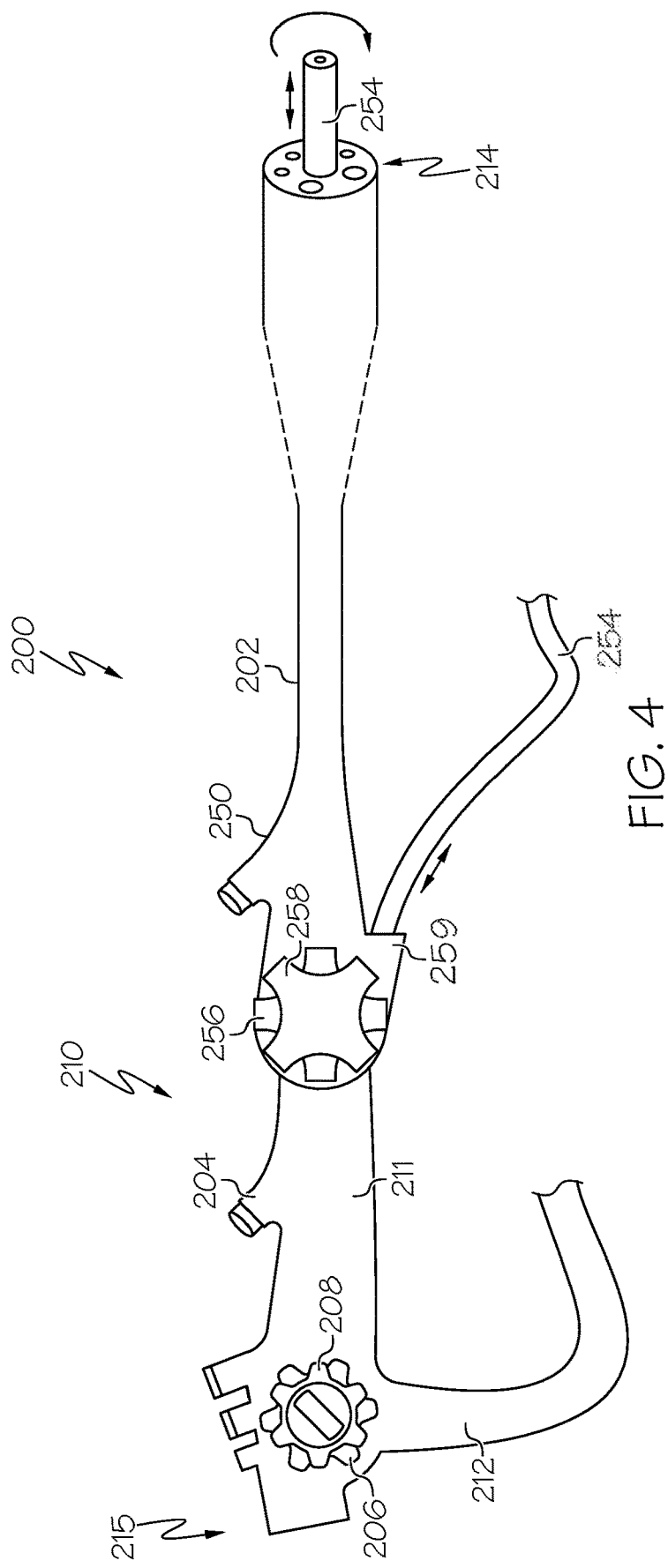
FIG. 4 is a side view of an alternate embodiment of a medical device, according to aspects of this disclosure.

FIG. 4 shows an exemplary embodiment of medical device 200. Device 200 includes a proximal end 215 and a distal end 214. A handle 210, including one or more actuators 206, 208, is at or adjacent to proximal end 215. Actuators 206, 208 may control articulation of the distal end 214 of medical device 200, via a connection between actuators 206, 208 and distal end 214, such as pulls wires. Articulation may be in two planes, such as up-down and left-right. Handle 210 further comprises one or more actuators 256, 258, which may control the articulation of the distal end of an internal shaft 254, to be described further herein. Like actuators 206, 208, actuators 256, 258 may control articulation of the distal end of shaft 254, via a connection between actuators 256, 258 and the distal end of shaft 254, such as pulls wires. Articulation may be in two planes, such as up-down and left-right. Actuators 256, 258 are positioned on handle 210 distally relative to actuators 206, 208. Actuators 256, 258 may be positioned on the same side of handle 210 (e.g. on the right-hand side of the handle during use), or may be on opposite sides of handle 210. The shape of handle 210 is defined by a handle shell 211.

Still referring to FIG. 4, a tube 212 may extend perpendicularly from at or near the proximal end 215 of device 200 relative to a central axis that extends from the proximal end 215 of device 200 to distal end 214. A proximal end of tube 212 may be coupled to handle 210, and a distal end of tube 212 may be connected to capital equipment such as a processor, pump, and/or other equipment commonly used in the art (not shown). Further, tube 212 may be comprised of multiple tubes (not shown) to enable irrigation and/or insufflation at the distal end 214.

Shaft 254 may extend through a lumen of shaft 202, into a distal end of handle 210, out of a port 259 proximate a distal end of the handle, away from handle 210, and connect to capital equipment such as a processor, pump, and/or other equipment commonly used in the art (not pictured). Shaft 254 may be configured such that a user may push or pull shaft 254 into or out of handle 210, respectively. Consequently, as a proximal portion of shaft 254 is pushed into handle 210, shaft 254 may extend past distal end 214, out of an opening at the distal face of shaft 202. As shaft 254 is pulled from handle 210, shaft 254 may retract into distal end 214.

A distal portion of shaft 254 may include an articulation joint or an otherwise sufficiently flexible portion to permit articulation of the distal portion of shaft 254. The portion of shaft 254 is connected to actuators 256, 258, so that rotation of actuators bends the distal portion in one or more planes (e.g. left-right and up-down). Similar to shaft 202, shaft 254 may be further comprised of one or more tubes and/or wires (not shown) to enable articulation, visualization, irrigation, and/or insufflation at distal end 214.

Handle 210 may also include one or more ports 204, 250, through which one or more accessory devices (not pictured) may be inserted. These accessory devices may include any of the instruments or tools described herein, including, as examples, guidewires, nets, baskets, cautery devices, etc. A proximal end of a lumen (e.g. working channel) (not pictured) may be attached to the distal end of the port 204, 250, and a distal end of a lumen may be attached to the distal end 214 of medical device 200. In embodiments, one or both of ports 204, 250 may be omitted from device 200.

Shaft 202 of medical device 200 may be a tube having sufficient length to access sites within the body. Additionally, shaft 202 may have sufficient flexibility to traverse tortuous anatomy. Shaft 202 can be made of flexible materials, rigid materials, or any combination thereof.

Aspects of the disclosure include methods of using device 200. To do so, the user may first introduce the distal end 214 of device 200 into a GI tract via a natural orifice. The orifice can be, for example, the nose, mouth, or anus, and the placement can be in any portion of the GI tract, including the esophagus, stomach, duodenum, large intestine, or small intestine. Delivery and placement also can be in other body lumens or organs reachable via the GI tract, any other natural opening or body tract, bodily incision, or through a delivery device, such as an endoscope or sheath. Once the desired site is accessed, the user can actuate one or more actuators, including knobs 206, 208, to control the articulation of the distal end 214. Further, a user may push shaft 254 into handle 210 to extend shaft 254 past the distal face of shaft 202. Conversely, a user may pull shaft 254 away from handle 210 to retract shaft 254 into shaft 202. One or more actuators, including actuators 256, 258, as described above, may control the distal end of shaft 254.

Figure 5:
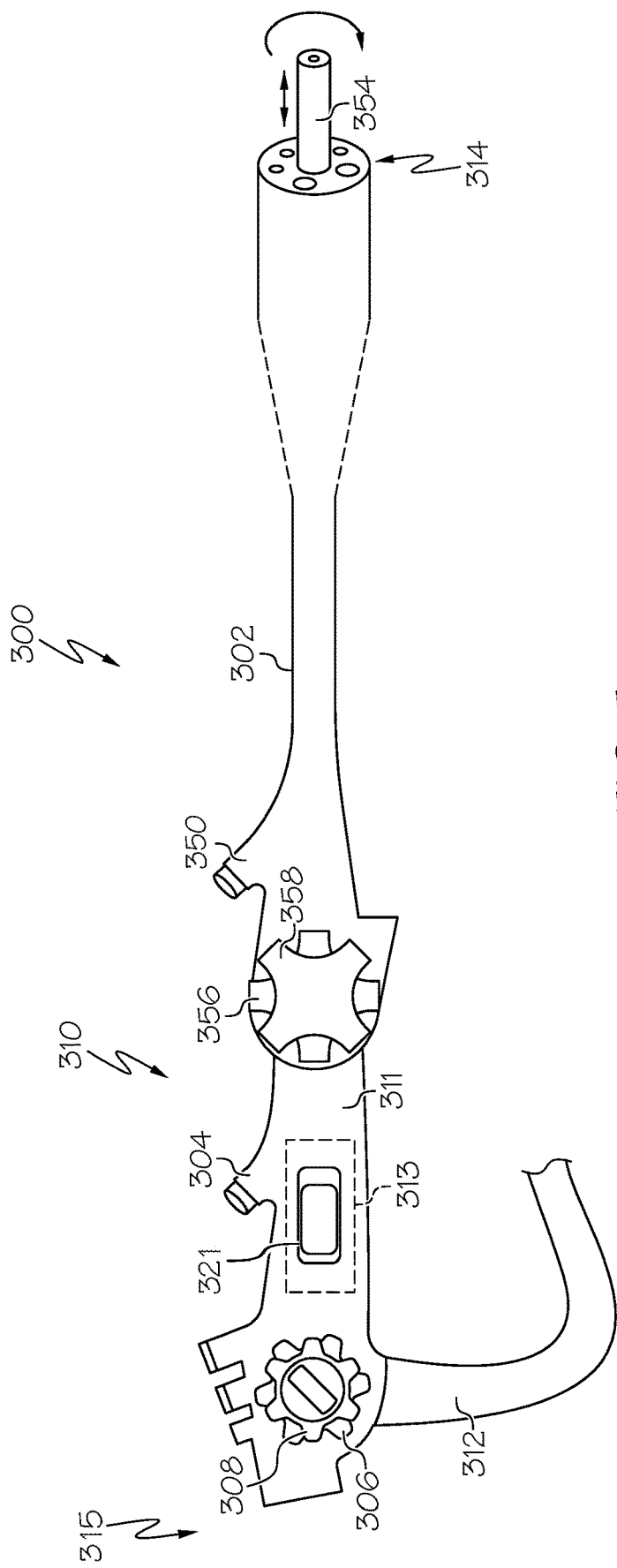
FIG. 5 is a side view of an alternate embodiment of a medical device, according to aspects of this disclosure.

FIG. 5 depicts an alternate embodiment of a medical device 300. Similar to FIG. 4, device 300 includes a proximal end 315 and a distal end 314. A handle 310, including one or more actuators 306, 308, is at or adjacent to proximal end 315. Actuators 306, 308 may control the distal end 314 of medical device 300, like actuators 206, 208 control the distal end 214 of medical device 200. Handle 310 further comprises one or more actuators 356, 358, which may control the articulation of the distal end of an internal shaft 354. Actuators 356, 358 are positioned on handle 310 distally relative to actuators 306, 308. Actuators 356, 358 may be positioned on the same side of handle 310 (e.g. on the right-hand side of the handle during use), or may be on opposite sides of handle 310. The shape of handle 310 is defined by a handle shell 311.

A distal portion of shaft 354 may include an articulation joint or an otherwise sufficiently flexible portion to permit articulation of the distal portion of shaft 354. That distal portion of shaft 354 is connected to actuators 356, 358, so that rotation of actuators bends the distal portion in one or more planes (e.g. left-right and up-down). Similar to how shaft 254 may be coupled to actuators 256, 258 to enable articulation of the distal end of shaft 254, shaft 354 may be coupled to actuators 356, 358 to enable articulation of the distal end of shaft 354. However, internal cabling, such as a camera cable, an irrigation tube, and/or an insufflation tube, may extend through a tube 312, to be described in further detail below.

Shaft 302 of medical device 300 may be a tube having sufficient length to access sites within the body. Additionally, shaft 302 may have sufficient flexibility to traverse tortuous anatomy. Shaft 302 can be made of flexible materials, rigid materials, or any combination thereof.

Still referring to FIG. 5, a tube 312 may extend perpendicularly (or approximately perpendicular) from at or near the proximal end 315 of device 300 relative to a central axis that extends from the proximal end 315 of device 300 to distal end 314. A distal end of tube 312 (not pictured) may be connected to capital equipment such as a processor, pump, and/or other equipment commonly used in the art (not shown). Further, tube 312 may be comprised of multiple tubes (not shown) to enable irrigation and/or insufflation at the distal end 314 of shaft 302. Tube 312 also may include a proximal portion of internal shaft 354 and/or a proximal portion of an internal camera cable (not pictured) of internal shaft 354. To extend internal shaft 354 from the distal end 314 of medical device 300, a user may actuate an actuator 321 of handle 310. Actuator 321 may be comprised of a mechanism similar to the subassembly 150 of FIGS. 2A and 2B, described previously. Alternatively, actuator 321 may be a knob, button, or any like actuator.

Figure 6A:
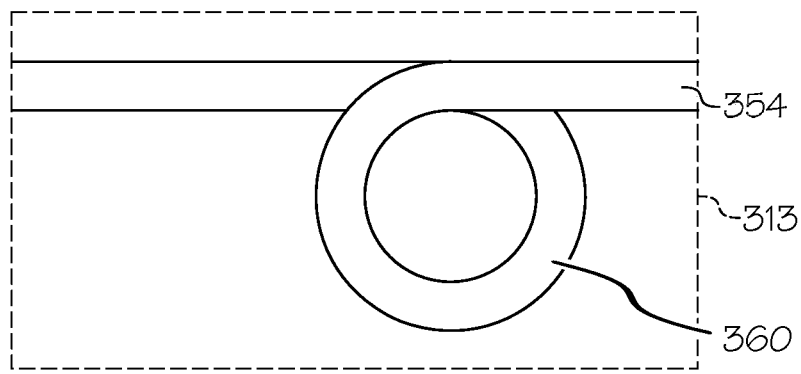
FIGS. 6A and 6B are internal sectional views of a camera cable of the medical device of FIG. 5 in the extended state (FIG. 6A) and in the retracted state (FIG. 6B), according to aspects of this disclosure.
Figure 6B:
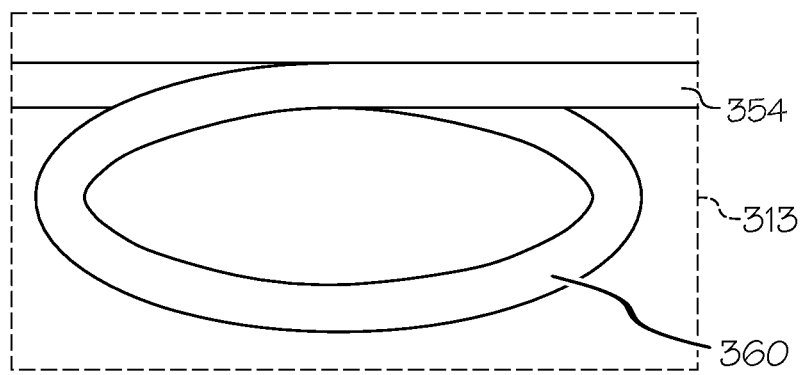

In an extended state of one embodiment, the actuation subassembly within section 313 may be arranged such that a looped configuration 360 of the proximal portion of shaft 354 may decrease when actuator 321 is actuated, as shown in section 313 of FIG. 6A. That proximal portion of shaft 254, having the looped configuration 360, is housed within handle shell 311. Conversely, to retract internal shaft 354 from the distal end 314 of medical device 300, a user may de-actuate actuator 321 such that the looped configuration 360 of the proximal portion of the shaft may increase, as shown in section 313 of FIG. 6B. The actuation and the de-actuation of actuator 321 may extend or retract a distal end of internal shaft 354 relative to distal end 314.

Referring again to FIG. 5, like ports 204, 250, handle 310 may also include one or more ports 304, 350, through which one or more accessory devices (not pictured) may be inserted.

Aspects of the disclosure include methods of using device 300. To do so, the user may first introduce the distal end 314 of device 300 into a GI tract via a natural orifice. The orifice can be, for example, the nose, mouth, or anus, and the placement can be in any portion of the GI tract, including the esophagus, stomach, duodenum, large intestine, or small intestine. Delivery and placement also can be in other body lumens or organs reachable via the GI tract, any other natural opening or body tract, bodily incision, or through a delivery device, such as an endoscope or sheath. Once the desired site is accessed, the user can actuate one or more actuators, including knobs 306, 308, to control the articulation of the distal end 314. Further, a user may actuate actuator 321 of handle 310 to extend internal shaft 354 past the distal face of shaft 302. Conversely, a user may de-actuate actuator 321 of handle 310 to retract internal shaft 354 into shaft 302. One or more actuators, including actuators 356, 358, as described above, may control the distal end of the internal shaft 354.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

Accordingly, various aspects discussed herein may help to improve the efficacy of treatment, for example, a procedure to treat a treatment site. Various aspects discussed herein may help to reduce and/or minimize the duration of the procedure, may reduce the risks of inadvertent manipulation by the user, and/or may help reduce risks of inadvertent contact with tissue or other material during delivery, repositioning, or usage of a medical device in the procedure.

While principles of this disclosure are described herein with reference to illustrative aspects for various applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

What is claimed is:

1. A medical device, comprising:
  a handle including a first actuator and a second actuator;
  a first shaft extending from a distal end of the handle, the
    first shaft including (1) a plurality of lumens extending therethrough, (2) a distal face, and (3) a longitudinal axis, wherein actuation of the first actuator articulates a distal portion of the first shaft;

a second shaft extending within a first lumen of the plurality of lumens, the second shaft axially movable relative to the first shaft to extend out of a distal opening of the first lumen and distally of the distal face, wherein actuation of the second actuator moves the second shaft relative to the first shaft; and a spring at a distal portion of the second shaft, wherein a proximal end of the spring is fixed axially relative to the first shaft, and wherein a distal end of the spring is fixed to the distal portion of the second shaft.

2. The medical device of claim 1, wherein axial movement of the second actuator in a first direction extends the second shaft relative to the first shaft; and axial movement of the second actuator in a second direction opposite the first direction retracts the second shaft relative to the first shaft.

3. The medical device of claim 1, further comprising a third actuator, wherein the third actuator is fixed axially relative to the first actuator, and wherein the third actuator prevents axial movement of the second shaft relative to the first shaft when the third actuator is depressed, and wherein the third actuator allows axial movement of the second shaft relative to the first shaft when the third actuator is released.

4. The medical device of claim 1, wherein a distal portion of the second shaft comprises a plurality of slots, wherein, when the distal portion is articulated, a proximal face of a first slot meets a distal face of a second slot.

5. The medical device of claim 1, wherein the spring provides a compressive force on the distal portion of the second shaft to articulate the second shaft when the second shaft extends from the distal face of the first shaft.

6. The medical device of claim 1, wherein the first actuator is proximal of the second actuator on the handle.

7. The medical device of claim 1, wherein a proximal portion of the second shaft is configured in a loop, the proximal portion positioned within the handle, and wherein, when the second shaft is extended past the distal face of the first shaft, a diameter of the loop decreases relative to a diameter of the loop when the second shaft is retracted into the first shaft.

8. The medical device of claim 1, wherein the handle comprises at least one port coupled to a proximal portion of a lumen of the first shaft.

9. The medical device of claim 1, wherein the first shaft comprises a camera at the distal face of the first shaft.

10. The medical device of claim 1, wherein the second shaft comprises a camera at a distal face of the second shaft.

11. The medical device of claim 1, wherein the distal face of the first shaft comprises one or more illumination features.

12. A medical device, comprising:
a handle including a first actuator and a second actuator;
a first shaft extending from a distal end of the handle, the first shaft including (1) a plurality of lumens extending therethrough and (2) a distal face, wherein actuation of the first actuator articulates a distal portion of the first shaft;
a second shaft having a longitudinal axis and extending within a first lumen of the plurality of lumens, the second shaft (1) axially movable relative to the first shaft to extend out of a distal opening of the first lumen and distally of the distal face and (2) rotatable about the longitudinal axis relative to the first shaft, wherein actuation of the second actuator selectively articulates a distal portion of the second shaft and rotates the second shaft relative to the first shaft; and
a spring at a distal portion of the second shaft providing a compressive force on the distal portion of the second shaft; and
wherein axial movement of the second actuator in a first direction extends the second shaft relative to the first shaft, axial movement of the second actuator in a second direction opposite the first direction retracts the second shaft relative to the first shaft.

13. The medical device of claim 12, further comprising a third actuator, wherein the third actuator is distal of the second actuator, and wherein the third actuator prevents axial movement of the second shaft relative to the first shaft when the third actuator is depressed, and wherein the third actuator allows axial movement of the second shaft relative to the first shaft when the third actuator is released.

14. The medical device of claim 12, wherein the spring provides a compressive force on the distal portion of the second shaft to articulate the second shaft when the second shaft extends from the distal face of the first shaft.

15. The medical device of claim 12, wherein a distal portion of the second shaft comprises a plurality of slots, wherein, when the distal portion is articulated, a proximal face of a first slot meets a distal face of a second slot.

16. The medical device of claim 12, wherein a distal face of the first shaft comprises a camera and one or more illumination features.

17. A medical device, comprising:
a handle including a first actuator and a second actuator, wherein the first actuator is proximal of the second actuator;
a first shaft extending from a distal end of the handle, the first shaft including (1) a plurality of lumens extending therethrough, (2) a distal face, and (3) a longitudinal axis, wherein actuation of the first actuator articulates a distal portion of the first shaft;
a second shaft extending within a first lumen of the plurality of lumens, the second shaft axially movable relative to the first shaft to extend out of a distal opening of the first lumen and distally of the distal face, wherein actuation of the second actuator moves the second shaft relative to the first shaft;
a first camera fixedly coupled to a distal face of the second shaft; and
a spring at a distal portion of the second shaft, wherein a proximal end of the spring is fixed axially relative to the first shaft, and wherein a distal end of the spring is fixed to the distal portion of the second shaft.

18. The medical device of claim 17, wherein the spring provides a compressive force on the distal portion of the second shaft to articulate the second shaft when the second shaft extends from the distal face of the first shaft.

19. The medical device of claim 17, wherein a distal face of the first shaft comprises a camera and one or more illumination features.

* * * * *